(12) United States Patent
Brickwood et al.

(10) Patent No.: US 7,264,139 B2
(45) Date of Patent: Sep. 4, 2007

(54) SENSOR DISPENSING DEVICE

(75) Inventors: David Brickwood, Godalming (GB); Graeme Maisey, Chessington (GB); Stuart Richard May, Kingston Upon Thames (GB)

(73) Assignee: Hypoguard Limited, Woodbridge (GB)

( * ) Notice: Subject to any disclaimer, the term of this patent is extended or adjusted under 35 U.S.C. 154(b) by 422 days.

(21) Appl. No.: 10/755,712

(22) Filed: Jan. 12, 2004

(65) Prior Publication Data

US 2004/0178216 A1 Sep. 16, 2004

Related U.S. Application Data

(60) Provisional application No. 60/441,503, filed on Jan. 21, 2003.

(30) Foreign Application Priority Data

Jan. 14, 2003 (GB) ................................ 0300765.5

(51) Int. Cl.
*B65H 59/02* (2006.01)
(52) U.S. Cl. ...................... 221/270; 221/268; 221/272; 221/273; 221/274; 221/275; 221/287
(58) Field of Classification Search ................. 221/197, 221/287, 268, 270, 272, 273–275
See application file for complete search history.

(56) References Cited

U.S. PATENT DOCUMENTS 3,836,033 A 9/1974 Mindt et al.

(Continued)

FOREIGN PATENT DOCUMENTS

| DE | 19639226 A1 | 9/1996 |
|---|---|---|
| EP | 0010456 A1 | 4/1980 |
| EP | 0016387 A1 | 10/1980 |
| EP | 0034049 A1 | 8/1981 |
| EP | 0057110 A2 | 8/1982 |
| EP | 0078636 A1 | 5/1983 |
| EP | 0095946 A1 | 12/1983 |
| EP | 0096095 A1 | 12/1983 |

(Continued)

OTHER PUBLICATIONS

Co-pending U.S. Appl. No. 11/028,942, filed Jan. 4, 2005, entitled "Biosensor And Method Of Manufacture".

(Continued)

*Primary Examiner*—Khoi H. Tran
(74) *Attorney, Agent, or Firm*—O'Keefe, Egan, Peterman & Enders LLP

(57) ABSTRACT

A sensor dispensing device (1) comprises a cartridge (2) having an outer casing (11) and a plurality of sensors (6) arranged one upon another in a stack. The cartridge has a first dispensing end (13) and a second opposing end (14) spaced a fixed distance apart, and the cartridge includes a first aperture (15) for the ejection of a sensor closest to the first end and a second aperture (16) opposed to the first aperture, for access by a pushing member (25). The first aperture and the second aperture are each provided with compliant sealing means (17) which are at least partly disposed outside the outer casing. The sealing means have first and second sealing surfaces which are capable of co-operating to releasably form a substantially moisture-tight seal when acted upon by suitable clamping forces. The device has a housing (34) for receiving the cartridge. For each of the compliant sealing means (17) there is a pair of clamping members (4, 33) for releasably clamping the sealing means to form a substantially moisture-tight seal. The device has a pushing member (25) for reversible insertion through the second aperture when the sealing means are not clamped, for pushing the sensor closest to the first end through the first aperture to a dispensed position.

28 Claims, 11 Drawing Sheets

U.S. PATENT DOCUMENTS

| | | |
|---|---|---|
| 3,838,033 A | 9/1974 | Mindt et al. |
| 3,979,274 A | 9/1976 | Newman |
| 3,992,158 A | 11/1976 | Przybylowicz et al. |
| 3,993,451 A | 11/1976 | Verbeck |
| 4,053,381 A | 10/1977 | Hamblen et al. |
| 4,137,495 A | 1/1979 | Brown |
| 4,142,863 A | 3/1979 | Covington et al. |
| 4,190,420 A * | 2/1980 | Covington et al. ............ 422/63 |
| 4,216,245 A | 8/1980 | Johnson |
| 4,225,410 A | 9/1980 | Pace |
| 4,233,029 A | 11/1980 | Columbus |
| 4,273,639 A | 6/1981 | Gottermeier |
| 4,301,412 A | 11/1981 | Hill et al. |
| 4,301,414 A | 11/1981 | Hill et al. |
| 4,303,887 A | 12/1981 | Hill et al. |
| 4,312,834 A | 1/1982 | Vogel et al. |
| 4,413,407 A | 11/1983 | Columbus |
| 4,418,148 A | 11/1983 | Oberhardt |
| 4,473,457 A | 9/1984 | Columbus |
| 4,476,149 A | 10/1984 | Poppe et al. |
| 4,490,216 A | 12/1984 | McConnell |
| 4,502,938 A | 3/1985 | Covington et al. |
| 4,545,382 A | 10/1985 | Higgins et al. |
| 4,591,550 A | 5/1986 | Hafeman et al. |
| 4,637,978 A | 1/1987 | Dappen |
| 4,654,127 A | 3/1987 | Baker et al. |
| 4,654,197 A | 3/1987 | Lilja et al. |
| 4,713,327 A | 12/1987 | Findlay et al. |
| 4,714,874 A | 12/1987 | Morris et al. |
| 4,849,623 A | 7/1989 | Osaki et al. |
| 4,897,173 A | 1/1990 | Nankai et al. |
| 4,900,405 A | 2/1990 | Otagawa et al. |
| 4,970,145 A | 11/1990 | Bennetto et al. |
| 4,978,503 A | 12/1990 | Shanks et al. |
| 5,108,564 A | 4/1992 | Szuminsky et al. |
| 5,118,404 A | 6/1992 | Saito |
| 5,120,420 A | 6/1992 | Nankai et al. |
| 5,128,015 A | 7/1992 | Szuminsky et al. |
| 5,141,868 A | 8/1992 | Shanks et al. |
| 5,160,278 A | 11/1992 | Johnson |
| 5,160,418 A | 11/1992 | Mullen |
| 5,185,256 A | 2/1993 | Nankai et al. |
| 5,228,972 A | 7/1993 | Osaka et al. |
| 5,231,028 A | 7/1993 | Mullen |
| 5,232,668 A | 8/1993 | Grant et al. |
| 5,271,896 A | 12/1993 | Jakubowicz et al. |
| 5,281,395 A | 1/1994 | Markart et al. |
| 5,288,636 A | 2/1994 | Pollmann et al. |
| 5,335,816 A | 8/1994 | Kaufman et al. |
| 5,335,822 A | 8/1994 | Kasper |
| 5,366,609 A | 11/1994 | White et al. |
| 5,395,504 A | 3/1995 | Saurer et al. |
| 5,407,554 A | 4/1995 | Saurer |
| 5,413,690 A | 5/1995 | Kost et al. |
| 5,429,735 A | 7/1995 | Johnson et al. |
| 5,508,171 A | 4/1996 | Walling et al. |
| 5,509,410 A | 4/1996 | Hill et al. |
| 5,525,297 A | 6/1996 | Dinger et al. |
| 5,526,120 A | 6/1996 | Jina et al. |
| 5,575,895 A | 11/1996 | Ikeda et al. |
| 5,616,222 A | 4/1997 | Maley et al. |
| 5,628,890 A | 5/1997 | Carter et al. |
| 5,660,791 A | 8/1997 | Brenneman et al. |
| 5,682,884 A | 11/1997 | Hill et al. |
| 5,708,247 A | 1/1998 | McAleer et al. |
| 5,727,548 A | 3/1998 | Hill et al. |
| 5,759,010 A | 6/1998 | Jacobs et al. |
| 5,770,028 A | 6/1998 | Maley et al. |
| 5,797,693 A | 8/1998 | Jaeger |
| 5,820,551 A | 10/1998 | Hill et al. |
| 5,985,116 A | 11/1999 | Ikeda et al. |
| 5,989,917 A | 11/1999 | McAleer et al. |
| 6,042,751 A | 3/2000 | Chan et al. |
| 6,168,957 B1 | 1/2001 | Matzinger et al. |
| 6,241,862 B1 | 6/2001 | McAleer et al. |
| 6,248,596 B1 | 6/2001 | Durst et al. |
| 6,258,229 B1 | 7/2001 | Winarata et al. |
| 6,287,451 B1 | 9/2001 | Winarata et al. |
| 6,338,790 B1 | 1/2002 | Feldman et al. |
| 6,436,256 B1 | 8/2002 | Williams et al. |
| 6,541,216 B1 | 4/2003 | Wilsey et al. |
| 6,565,738 B1 | 5/2003 | Henning et al. |
| 6,627,058 B1 | 9/2003 | Chan |
| 6,656,702 B1 | 12/2003 | Yugawa et al. |
| 6,863,800 B2 | 3/2005 | Karinka et al. |
| 6,997,343 B2 * | 2/2006 | May et al. .................. 221/232 |
| 2002/0057993 A1 | 5/2002 | Maisey et al. |
| 2002/0146835 A1 | 10/2002 | Modzelewski et al. |
| 2003/0116583 A1 | 6/2003 | Pugh |
| 2005/0281706 A1 * | 12/2005 | Funke et al. .................. 422/63 |

FOREIGN PATENT DOCUMENTS

| | | |
|---|---|---|
| EP | 0121385 A1 | 10/1984 |
| EP | 0127958 | 12/1984 |
| EP | 0136362 A1 | 4/1985 |
| EP | 0170375 B1 | 2/1986 |
| EP | 0171148 A1 | 2/1986 |
| EP | 0186286 A1 | 7/1986 |
| EP | 0200539 B1 | 11/1986 |
| EP | 0212314 A2 | 3/1987 |
| EP | 0215446 A2 | 3/1987 |
| EP | 0225061 A1 | 6/1987 |
| EP | 0230472 A1 | 8/1987 |
| EP | 0239222 A1 | 9/1987 |
| EP | 0255291 A1 | 2/1988 |
| EP | 0267724 A1 | 5/1988 |
| EP | 0271102 A2 | 6/1988 |
| EP | 0359831 A1 | 3/1990 |
| EP | 0170375 B1 | 5/1990 |
| EP | 0373413 A1 | 6/1990 |
| EP | 375363 A2 | 6/1990 |
| EP | 0115873 B1 | 11/1990 |
| EP | 0471986 A2 | 2/1992 |
| EP | 0127958 B1 | 3/1992 |
| EP | 0593096 A2 | 4/1994 |
| EP | 0636879 A2 | 2/1995 |
| EP | 0645627 A1 | 3/1995 |
| EP | 0732590 A3 | 1/1996 |
| EP | 0738666 B1 | 4/1996 |
| EP | 0732590 A2 | 9/1996 |
| EP | 0738666 A2 | 10/1996 |
| EP | 0771867 A2 | 5/1997 |
| EP | 0811843 A2 | 6/1997 |
| EP | 0885591 A2 | 12/1998 |
| EP | 0969097 A2 | 7/1999 |
| GB | 1318815 | 5/1973 |
| GB | 2001443 A | 1/1979 |
| GB | 2090659 A | 7/1982 |
| GB | 2227010 A | 7/1990 |
| GB | 2307231 A | 5/1997 |
| GB | 2337122 A | 11/1999 |
| GB | 2351153 A | 12/2000 |
| JP | 56163447 A | 12/1981 |
| JP | 59-40145 | 3/1984 |
| JP | 62030962 A | 2/1987 |
| JP | 62-237348 | 10/1987 |
| JP | 63-3248 | 1/1988 |
| JP | S61-146392 | 1/1988 |
| JP | 63-58149 | 3/1988 |
| JP | 63-137559 | 6/1988 |
| JP | 63-144245 | 6/1988 |
| JP | 63-144246 | 6/1988 |
| JP | 63-144247 | 6/1988 |

| | | |
|---|---|---|
| JP | 63-317096 | 12/1988 |
| JP | 64-23152 | 1/1989 |
| JP | 64-23153 | 1/1989 |
| JP | 64-23154 | 1/1989 |
| JP | 1-14746 | 5/1989 |
| JP | 1-114747 | 5/1989 |
| JP | 1-134242 | 5/1989 |
| JP | 1-134243 | 5/1989 |
| JP | 1-134244 | 5/1989 |
| JP | 1-212345 | 8/1989 |
| JP | 1-253648 | 10/1989 |
| JP | 1-291153 | 11/1989 |
| JP | 2-62952 | 3/1990 |
| JP | 04326054 | 11/1992 |
| JP | 11344460 A | 12/1999 |
| WO | WO88/03270 | 5/1988 |
| WO | WO89/08713 | 9/1989 |
| WO | WO92/14836 | 9/1992 |
| WO | WO9215861 A1 | 9/1992 |
| WO | WO94/10558 | 11/1993 |
| WO | WO9607907 A1 | 3/1996 |
| WO | WO97/30344 | 8/1997 |
| WO | WO98/19159 | 5/1998 |
| WO | WO98/55856 | 12/1998 |
| WO | WO99/05966 | 2/1999 |
| WO | WO99/13100 | 3/1999 |
| WO | WO 01/23885 A1 | 8/1999 |
| WO | WO00/78992 | 12/2000 |
| WO | WO01/46457 A2 | 6/2001 |
| WO | WO 02/08753 A2 | 1/2002 |
| WO | WO 02/18940 A2 | 3/2002 |
| WO | WO02/057766 A2 | 7/2002 |
| WO | WO03/042691 A1 | 5/2003 |
| WO | WO2004/008130 A1 | 1/2004 |

OTHER PUBLICATIONS

Co-pending U.S. Appl. No. 11/028,941, filed Jan. 4, 2005, entitled "Biosensor And Method Of Manufacture".

Co-pending U.S. Appl. No. 10/094,501, filed Mar. 8, 2002, "Test Member Orientation".

Co-pending U.S. Appl. No. 10/233,265, filed Aug. 30, 2002, "Sensor Dispensing Device".

Co-pending U.S. Appl. No. 10/265,087, filed Oct. 4, 2002, "Test Meter Calibration".

Co-pending U.S. Appl. No. 10/089,048, filed Mar. 25, 2002, "Test Device".

Karl Schugerl et al., "Online-ProzeBanalyse In Bioreaktoren", No. 9, Germany, Sep. 1987.

Co-pending U.S. Appl. No. 10/617,262, filed Jul. 10, 2003, entitled "Enzyme Electrodes And Method of Manufacture".

* cited by examiner

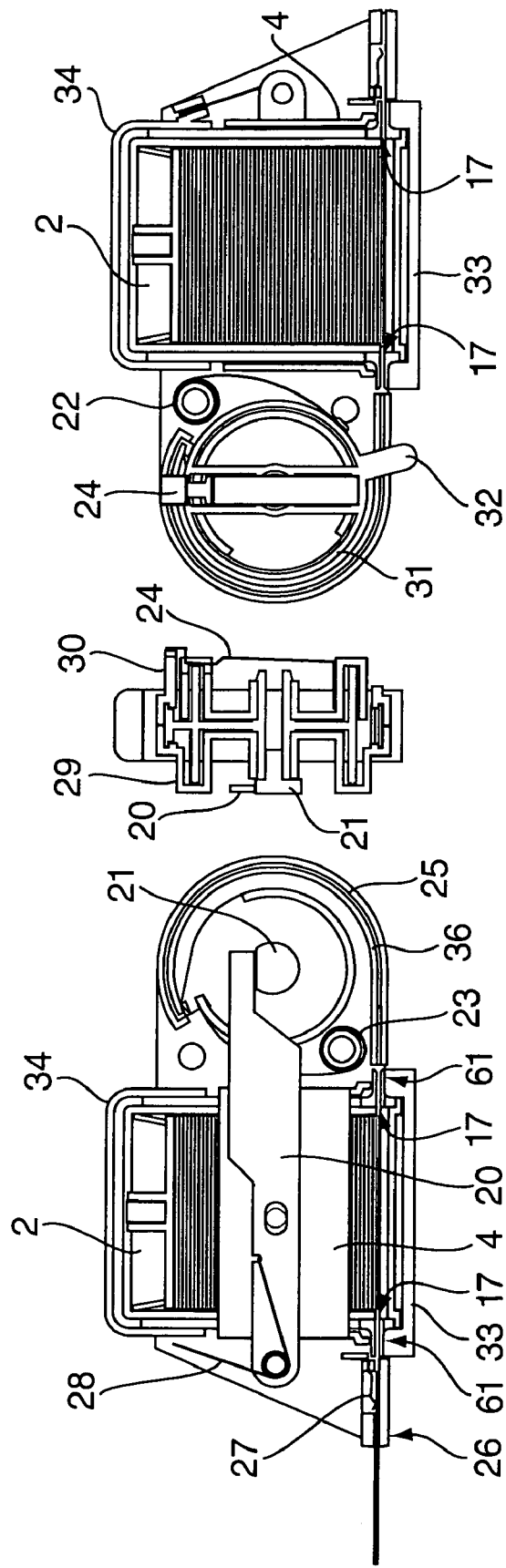

SENSOR DISPENSING DEVICE

This application claims priority to now abandoned U.S. provisional application Ser. No. 60/441,503 filed on Jan. 21 2003, which is entitled "SENSOR DISPENSING DEVICE" the disclosure of which is incorporated herein by reference. This application also claims priority to United Kingdom patent application serial number 0300765.5 filed Jan. 14, 2003, which is entitled "SENSOR DISPENSING DEVICE" the disclosure of which is also incorporated herein by reference.

BACKGROUND OF THE INVENTION

1. Field of the Invention

The present invention relates to a device for dispensing sensors for measuring the concentration of an analyte in a fluid sample (notably glucose in whole blood), and to a cartridge containing sensors for use in the device. The invention also provides a meter incorporating the dispensing device.

2. Description of the Prior Art

Diabetics regularly need to test samples of their blood to determine the levels of blood glucose. In one known type of test system, disposable sensors are used to test the blood. The sensors typically take the form of test strips which are provided with a reagent material that will react with blood glucose to produce an electrical signal. Conductive tracks on the test strip relay the electrical signal to a meter which displays the result. After a sample of blood has been applied to the test strip and the measurement has been taken, the test strip is disposed of. Examples of test devices with test strip dispensers are described in U.S. Pat. No. 5,660,791, and European Patent Application Numbers 0 732 590, 0 738 666, and 0 811 843.

A problem with test strips is that they have only a limited shelf life, and exposure of test strips to the atmosphere further reduces the shelf life.

In DE 196 39 226 A1 it is proposed to provide a test device with a cartridge that may have a plurality of chambers containing test strips, each of which chambers may be individually sealed to preserve the shelf life of the strips therein. A user removes the seal for each chamber when required, and a timing circuit may be activated either by the user or when the cartridge is pushed into the device. After a set time period has elapsed, an alarm or other indication reminds the user that the time period for using the strips has elapsed. WO 02/08753 describes a blood glucose meter which has test strips arranged in a plurality of stacks in a magazine. Each stack is individually sealed, and the stack's seal is broken automatically when the magazine moves to a location where a test member can be dispensed by means of a suitable pusher.

It has been proposed in WO 94/10558 to provide a stack of disposable sensors in a cylindrical housing, the stack being urged towards a test station to form a liquid-proof seal. In WO 02/18940 there is disclosed a blood glucose test meter in which a stack of test strips in a replaceable cartridge are sealed against a rotatable transport member which is adapted to receive a single test strip and rotatably transport the test strip while maintaining a seal around the cartridge.

A problem with such systems is that the sealing means may wear with repeated use and the quality of the seal may consequently be reduced.

U.S. Pat. No. 5,759,010 discloses a cartridge for dispensing slide test elements of the kind which have an opening for liquid access. The cartridge is provided with an internal cover plate which is biased to make a sealing contact with the opening so as to protect the inside of the opening from atmospheric moisture before the slide is dispensed. Such an arrangement is less desirable for test members in which the reagents are not located in an opening of a moisture-impermeable slide member because it is difficult to make a reliable seal around the reagents. Friction between the reagent layer and the plate may also tend to abrade the reagent layer.

It is an object of the present invention to provide an improved test device. It is a further object of the invention to provide an improved dispenser for sensors for use in measuring analyte concentration in an applied fluid.

SUMMARY OF THE INVENTION

According to an aspect of the present invention there is provided a sensor dispensing device for dispensing sensors for testing of analyte concentration in a fluid to be applied thereto, the device comprising:

a cartridge having an outer casing and a plurality of sensors arranged one upon another in a stack therein;

the cartridge having a first dispensing end and a second opposing end spaced a fixed distance apart, and the cartridge including a first aperture for the ejection of a sensor closest to the first end and a second aperture opposed to the first aperture, for access by a pushing member;

wherein the first aperture and the second aperture are each provided with compliant sealing means which are carried by the cartridge and which are at least partly disposed outside the outer casing, the sealing means having first and second sealing surfaces which are capable of co-operating to releasably form a substantially moisture-tight seal when acted upon by suitable clamping forces;

the device further comprising:

a housing for receiving the cartridge;

for each of the said compliant sealing means, a pair of clamping members for releasably clamping the sealing means to form a substantially moisture-tight seal; and a pushing member for reversible insertion through the second aperture when the sealing means are not clamped, for pushing the sensor closest to the first end through the first aperture to a dispensed position.

By providing the sealing means on the cartridge, problems of wear are reduced because the seals are replenished each time the cartridge is replaced.

In a preferred embodiment each of the sealing means comprises a tube of a natural or synthetic rubber material. Suitable materials include styrene-ethylene-butylene-styrene (SEBS), for example Thermoflex™, ethylene-propylene-diene monomer (EPDM) terpolymer, optionally alloyed with other materials such as polypropylene. Preferred materials are thermoplastic elastomers, for example Santoprene™, a nitrile rubber mixed with polypropylene, or thermoplastic polyurethane elastomers, for example Pellethane™. A preferred material is a mixture of Thermoflex™ 45A with Nourymix™ SP E60 antistatic/slip agent (from Akzo Nobel Chemicals). Nourymix™ SP E60 comprises 80% of a rapeseed oil-based erucamide (13-docosenamide) on a polypropylene carrier. The additive helps to prevent sticking of the tubular elastomer after being clamped for a length of time. The concentration of Nourymix™ is preferably in the range 0.2 to 5%, notably about 3%. Each tube may be disposed through its associated aperture and be a close fit for this aperture. Thus, when the tubes are suitably clamped or nipped the inside of the cartridge is sealed from moisture.

The compliant sealing means may alternatively comprise a pair of opposed sealing surfaces of rubber or other elastomeric material which do not form part of a tube. The pushing member passes between two sealing surfaces on the cartridge when it enters the second aperture, and a sensor passes between two sealing surfaces on the cartridge when it is dispensed from the cartridge. For convenience the invention will be described with reference to the use of a tubular rubber sealing member, but it will be understood that the invention is not limited to this embodiment.

A separate pair of clamping members may be provided for each sealing member. However, in a preferred embodiment a single pair of clamping members may serve to clamp both sealing members. For simplicity it is preferred that one clamping member is fixed while the other is movable, although both clamping members could of course be movable if desired. It is preferred that both clamping members of the pair are provided in or on the housing; however, it would be possible to provide one clamping member (notably, a fixed clamping member) on the cartridge.

The pusher is preferably flexible so that it can be coiled on a drum or other suitable support so that the device may be made compact. A running guide may be incorporated into the cartridge mouldings so that the pusher will be supported throughout its travel through the cartridge to facilitate reliable dispensing of a thin test strip. Provision of a guiding slot creates the potential for the pusher to be moulded as a single component, for example of acetal.

The sensor in the dispensed position may be taken by the user and used in a conventional test meter. In a preferred embodiment, however, the device further comprises signal-reading means for determining the concentration of an analyte in an applied sample according to a signal generated by the sensor in the dispensed position. The signal-reading means may comprise electronic circuitry for measuring an electric signal generated by the sensor in response to analyte concentration in an applied sample. With the sensor in the dispensed position its electrodes engage with contacts connected to the circuitry, in known manner. Alternatively, the signal-reading means may measure an optical change in the sensor, for example a colour change. Many suitable signal-reading means are known to those skilled in the art. With the inclusion of signal-reading means the device is a meter for measuring analyte concentration in a fluid. For convenience hereinafter the invention will be described with reference to its embodiment in a blood glucose meter, but it will be understood that the invention is not limited to this application.

The cartridge may be sold as a separate item for refilling the sensor dispensing device or meter. Accordingly, another aspect of the invention provides a cartridge comprising:

an outer casing and a plurality of sensors arranged one upon another in a stack therein, each sensor being for testing of analyte concentration in a fluid to be applied thereto;

the cartridge having a first dispensing end and a second opposing end spaced a fixed distance apart, and the cartridge including a first aperture for the ejection of a sensor closest to the first end and a second aperture opposed to the first aperture, for access by a pushing member;

wherein the first aperture and the second aperture are each provided with compliant sealing means which are at least partly disposed outside the outer casing, the sealing means having first and second sealing surfaces which are capable of co-operating to releasably form a substantially moisture-tight seal when acted upon by suitable clamping forces.

The housing may contain a desiccant to absorb moisture. In a preferred embodiment, the cartridge inner assembly or a component thereof, for example a sprung follower, may be formed from a desiccant plastics material. Suitable desiccant plastics materials are known in the art and may be obtained from CSP Technologies, Bourne End, Bucks, UK.

It is preferred that spring means are provided in the cartridge for urging the stack of sensors towards the dispensing end. Any suitable spring means may be used and are well known to those skilled in the art. Examples are coil or compression springs, elastic members, or pneumatic or motorised pushing members. It is preferred that the spring means are constant tension springs to provide controlled movement of the stack within the housing.

The cartridge may optionally contain a calibration strip which will be the first strip to be dispensed, to enable calibration of the meter for the batch of strips therein.

Other aspects and benefits of the invention will appear in the following specification, drawings and claims.

BRIEF DESCRIPTION OF THE DRAWINGS

The invention will now be further described, by way of example only, with reference to the following drawings in which:

FIGS. 6-8 are part-sectional views through the meter of FIG. 3 from above the meter, from the handle end of the meter, and from below the meter respectively;

DETAILED DESCRIPTION

Figure 3:
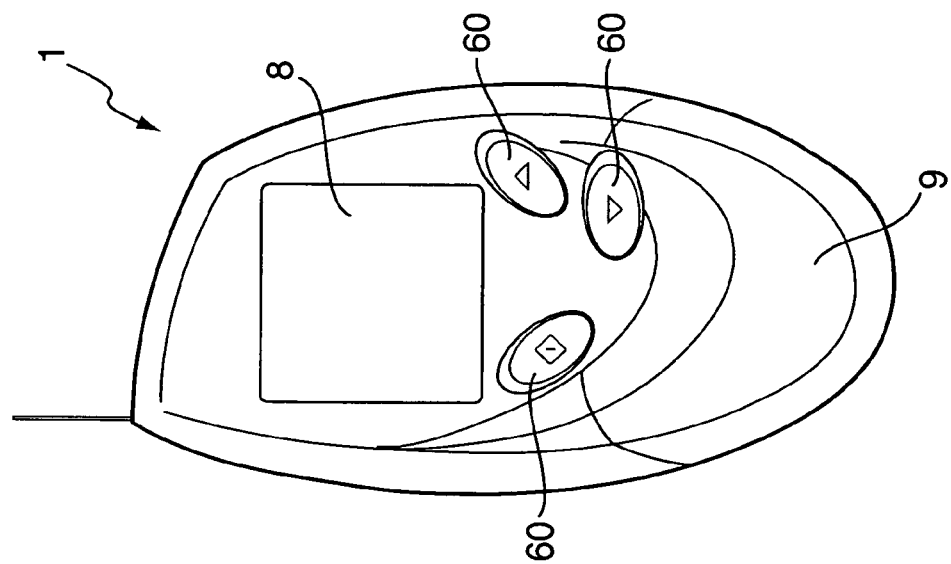
FIG. 3 is a top view of the blood glucose meter of FIGS. 1 and 2.

In the embodiments illustrated in the drawings, parts which perform the same function will be denoted by the same numbers.

Figure 2:
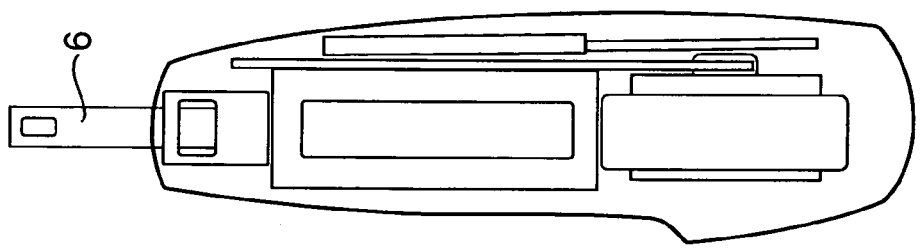
FIG. 2 is a simplified cutaway view from the right side of the meter of FIG. 1.
Figure 1:
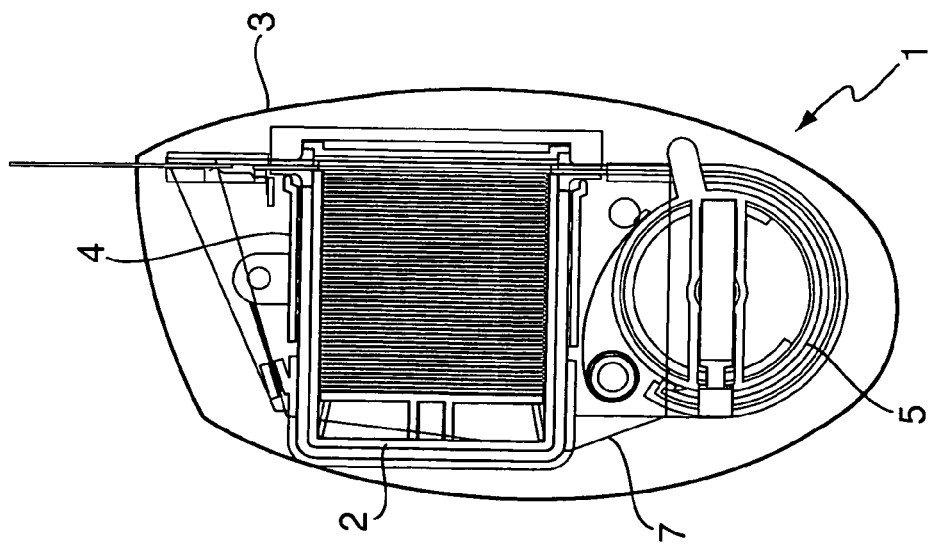
FIG. 1 is a sectional view from underneath a blood glucose meter according to a first embodiment of the invention.

The blood glucose meter 1 shown in FIGS. 1 to 3 comprises an outer casing 3 which houses a cartridge 2 and a delivery mechanism 5 for dispensing test strips 6 from the cartridge 2. The casing 3 also houses a moveable clamp 4 for sealing the inside of the cartridge 2 from atmospheric moisture, as will be described in more detail below. The external features of the meter 1 comprise control buttons 60 for controlling the operation of the meter, an LCD 8 for displaying user instructions, results and other data, and an external handle 9 for actuating the delivery mechanism. A control PCB 7 is operably connected to the LCD 8 and buttons 60. The meter 1 of FIGS. 1-3 is shown with a test strip 6 in a dispensed position ready to receive a drop of blood.

Figure 5:
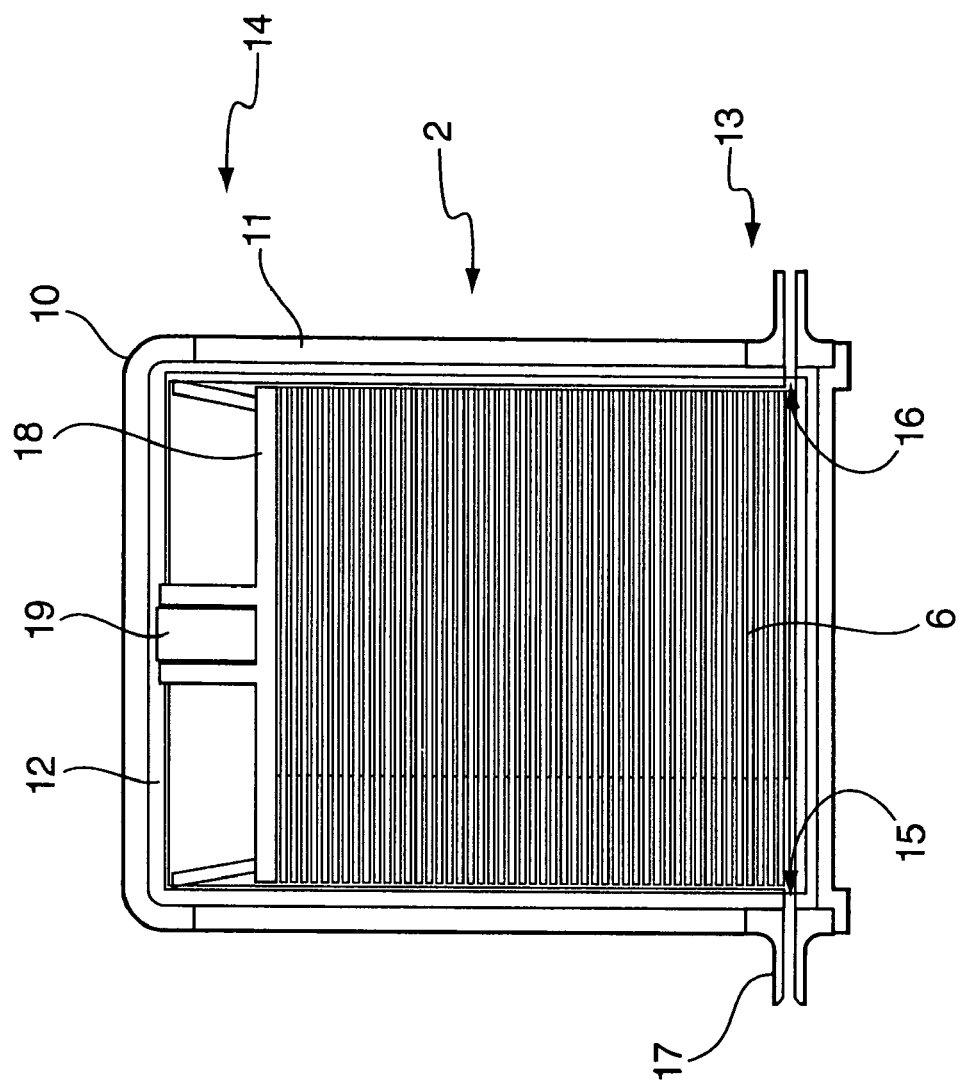
FIG. 5 is sectional view along the lines I-I of FIG. 4.
Figure 4:
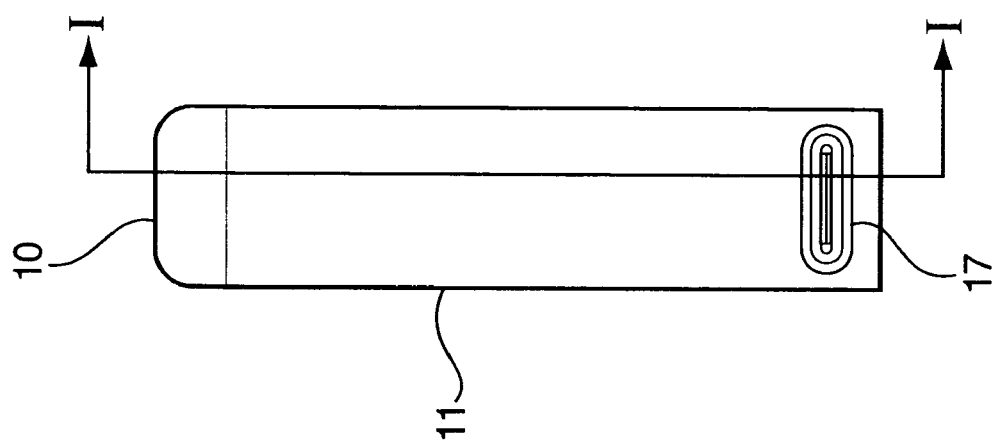
FIG. 4 is an end elevation view of a cartridge for the meter of FIGS. 1 to 3 in accordance with an embodiment of a further aspect of the invention.

Referring now to FIGS. 4 and 5, the cartridge 2 has an inner assembly 12 and an outer casing 11, in this example formed from polypropylene, sealingly covered by a cap 10. The cartridge has a first, dispensing, end 13 and an opposing end 14 which in this embodiment includes the cap 10. The cap 10 may be welded to the remainder of the outer casing, for example by ultrasonic welding, to form a fluid-tight bond. Instead of a cap, the outer casing may be closed by foil, for example of aluminium, or other suitable sealing member.

Figure 9:
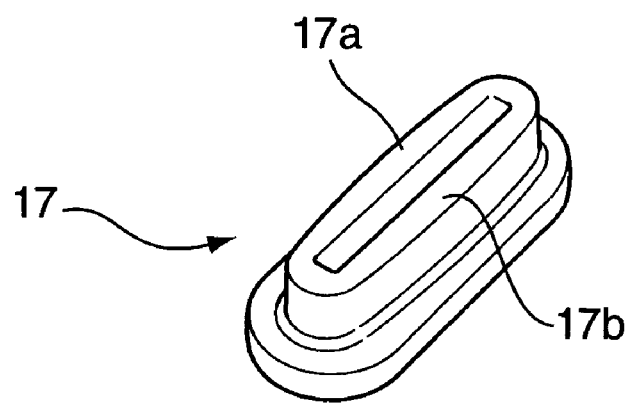
FIG. 9 is a perspective view of an embodiment of a rubber sealing member for use in the invention.

A stack of test strips 6 is housed in the cartridge inner assembly 12, and the strips 6 are urged towards the dispensing end by a constant tension spring 19 which acts on a follower 18. At the dispensing end 13 there are opposed first 15 and second 16 apertures, each of which is provided in this embodiment with a co-moulded tubular rubber sealing member 17, as best shown in FIG. 9. The sealing members 17 comprise a first sealing lip 17a and a second sealing lip 17b, each sealing lip providing a sealing surface. In this embodiment, the sealing surfaces are provided as part of a single tubular member 17, but they could alternatively be separately provided. When the sealing members 17 are open they permit a pusher to be inserted through one aperture to push a test strip 6 through the other aperture. When the sealing members 17 are clamped shut, the inside of the outer casing 11 is substantially sealed off from atmospheric moisture. The cartridge 2 will be kept in a moisture-tight container (not shown) until immediately prior to its insertion into the meter 1.

Figure 19:
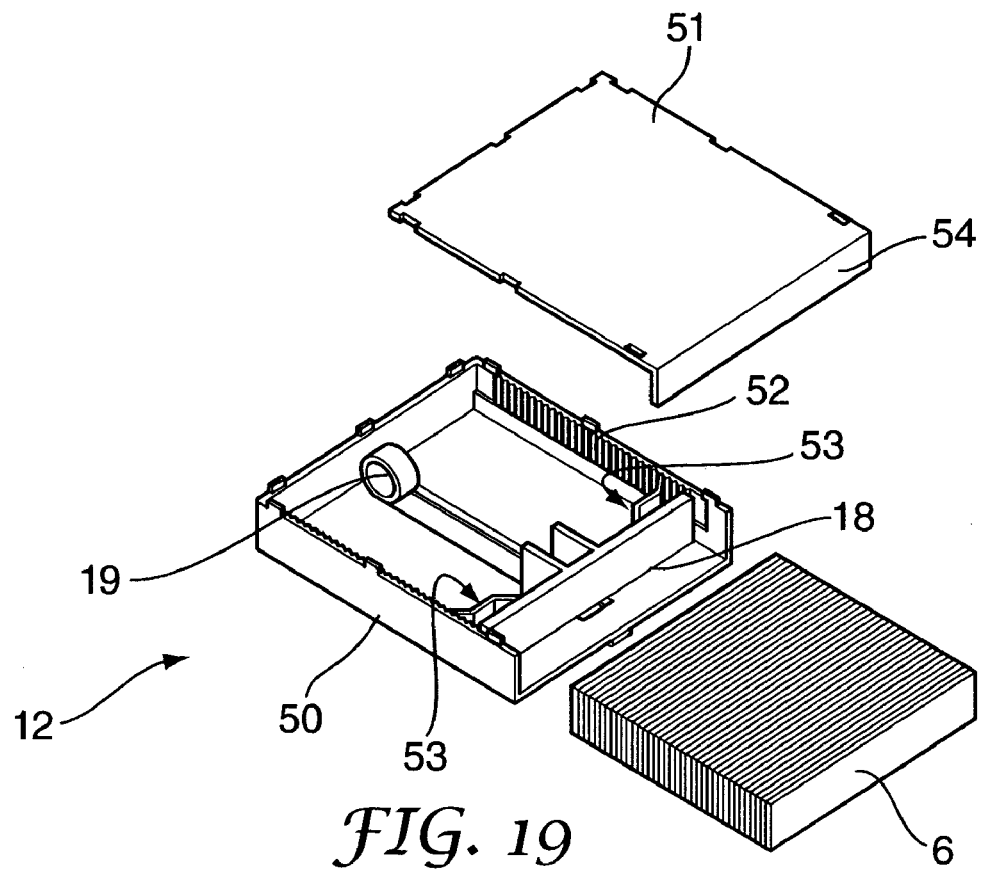
FIG. 19 is an exploded view of one embodiment of a cartridge inner assembly for the cartridge of FIG. 5.
Figure 20:
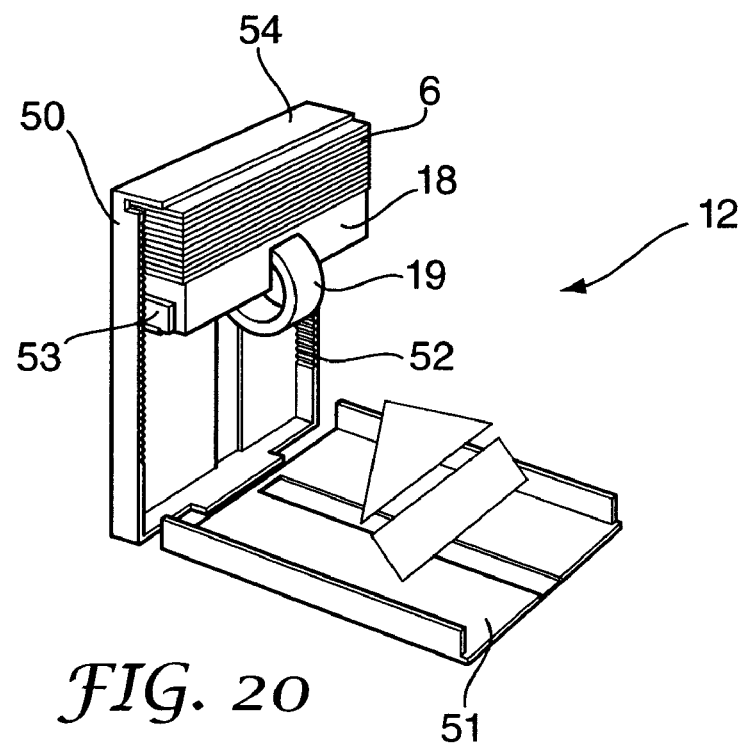
FIGS. 20 and 21 illustrate stages in the assembly of an alternative embodiment of a cartridge inner assembly for the cartridge of FIG. 5.
Figure 21:
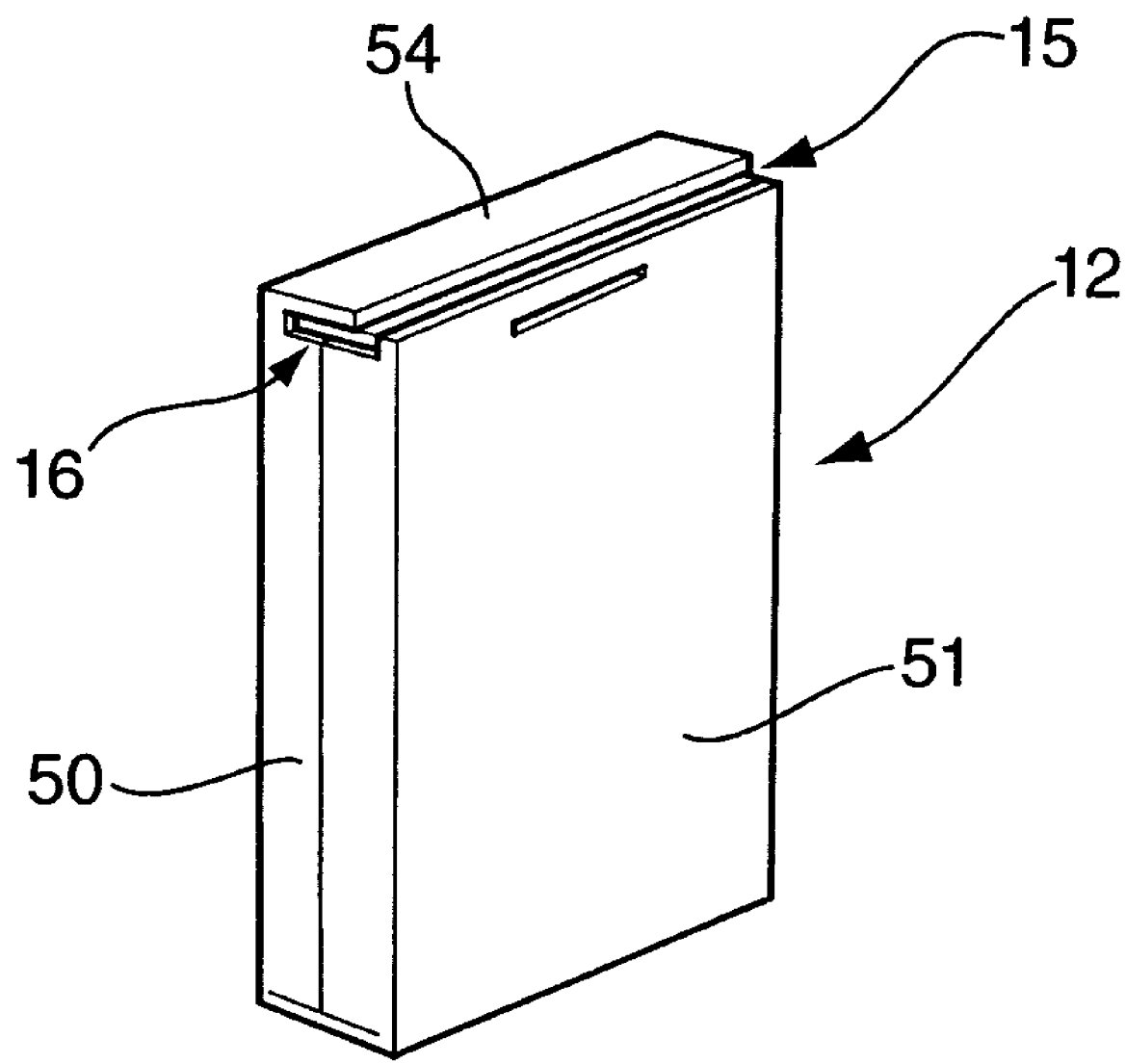

One way of manufacturing the cartridge inner assembly 12 is illustrated in the exploded diagram shown in FIG. 19. The walls of the cartridge inner assembly 12 are formed from a base member 50 and a closure member 51. Two opposed upstanding walls of the base member 50 are provided with a series of ridges 52 in which fit arms 53 of the follower 18. The ridges 52 and arms 53 comprise ratchet means which are profiled to permit movement of the follower 18 in one direction only, towards the stack of test strips 6. During assembly, the follower 18 is located near to the spring 19 to permit the stack of strips 6 to fit in the base member 50. The closure member 51 is snap-fitted on the base member 50 to form the cartridge inner assembly 12. A lip 54 on the closure member 51 provides a stop member which limits outward travel of the strips 6. There is a sufficient gap between the lip 54 and the adjacent walls of the base member 50 (which define opposed openings of the housing) to permit a single strip 6 to slide out axially. An alternative design of cartridge inner assembly 12 is shown in FIGS. 20 and 21. Here, the stop member 54 is provided on the base member 50.

Referring now to FIGS. 6-8, the working parts of the meter 1 are mounted on a chassis comprising a first chassis member 29 and a second chassis member 30. The cartridge 2 is received in a cartridge-receiving housing 34 in the meter casing 3. A lid 33, is closed over the dispensing end of the cartridge 2 and provides a shoulder 61 on which the tubular sealing members 17 rest. The clamp 4 is urged towards the lid 33 by a clamping spring 28. The clamp 4 is operatively connected to by a clamp arm 20 to a rotatable arm lift cam 21. In the rest position shown in FIG. 6, the clamp 4 and shoulder 61 provide a pair of clamping members. The bottom edges of the clamp 4 exert a clamping force on the tubular sealing members 17 so as to clamp the sealing members 17 between the pair of clamping members 4, 61, thereby providing a substantially fluid-tight seal to protect the inside of the cartridge 2 from the external atmosphere. The delivery mechanism comprises a pusher drum 36 on which is wound an axially elongate pusher 25, and a drive drum 31 which has a drive handle 32 operatively connected to the external handle 9 of the meter. A latch spring 24 is provided on the drive drum 31 for releasably engaging the drive drum 31 with the pusher drum 36. It will be understood that the drive drum and the pusher drum need not be hollow, and could comprise solid cylinders, wheels, discs or the like. It is preferred that the drums are substantially circular in cross section, but other shapes such as an oval could also be used.

Figure 16:
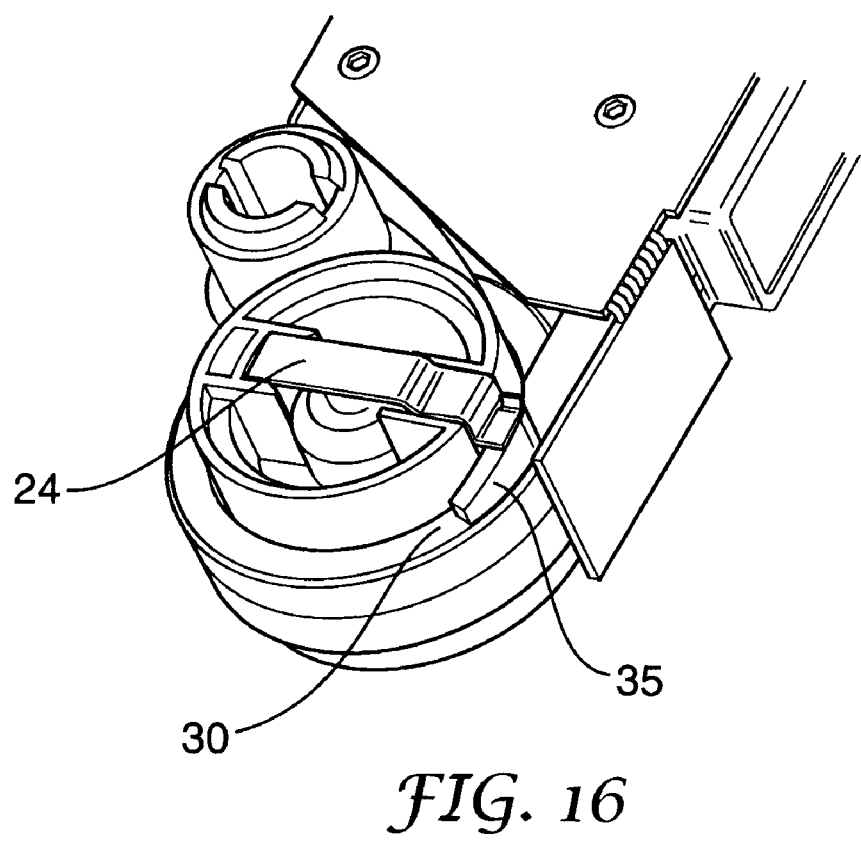

In the rest position the latch spring 24 is disengaged by a ramp 35 which is part of the second chassis member 30, as best shown in FIG. 16. As the user operates the external handle 9, the handle 32 of the drive drum turns the drive drum 31. The drive drum 31 is free to turn through a set angle with the latch spring 24 turning with it. A drive spring 22, which connects the drive drum 31 directly or indirectly to the chassis, is wound up. Nothing happens to the pusher 25 during the initial turning as it is held with a one-way ratchet feature. If the user releases the drive drum at this point the mechanism will return to the rest position without dispensing a test strip 6. At the "point of no return" the latch spring 24 drops into a slot on the pusher drum 36, effectively locking the two drums together. At this point the pusher 25 is in its rest position. When the user lets go the handle 9, the drive drum 31 and pusher drum 36 are forced to rotate by the wound-up drive spring 22. During this rotation three things happen:

the arm lifting cam 21 lifts the clamp arm 20 to open the tubular sealing members 17 (FIG. 8);

the flexible pusher 25 forces a test strip 6 from the cartridge 2 to a dispensed position under meter contacts 27 within a contact block 26; and a return spring 23, which connects the pusher drum 36 directly or indirectly to the chassis, is wound up.

Figure 15:
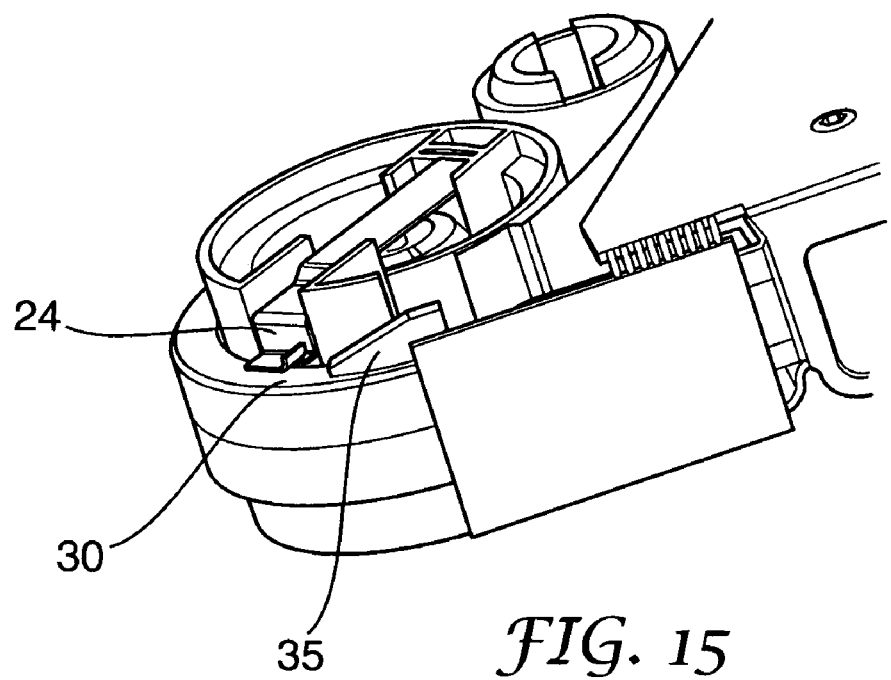
FIGS. 15 and 16 are perspective views showing details of the latch spring mechanism of an embodiment of the invention.

At the end of the rotation of the drive drum 31, the latch spring 24 is lifted out of the slot in the pusher drum 36 by the ramp 35. The relative positions of the latch spring 24 before and after engagement with the ramp 35 are illustrated in FIGS. 15 and 16 respectively.

When the pusher drum 36 is released from the drive drum 31 it returns to its rest position by the action of the return spring 23. At the end of this rotation the arm lift cam 21 permits the clamp arm 20 to drop and re-establish a clamping force across the sealing members 17.

Figure 12:
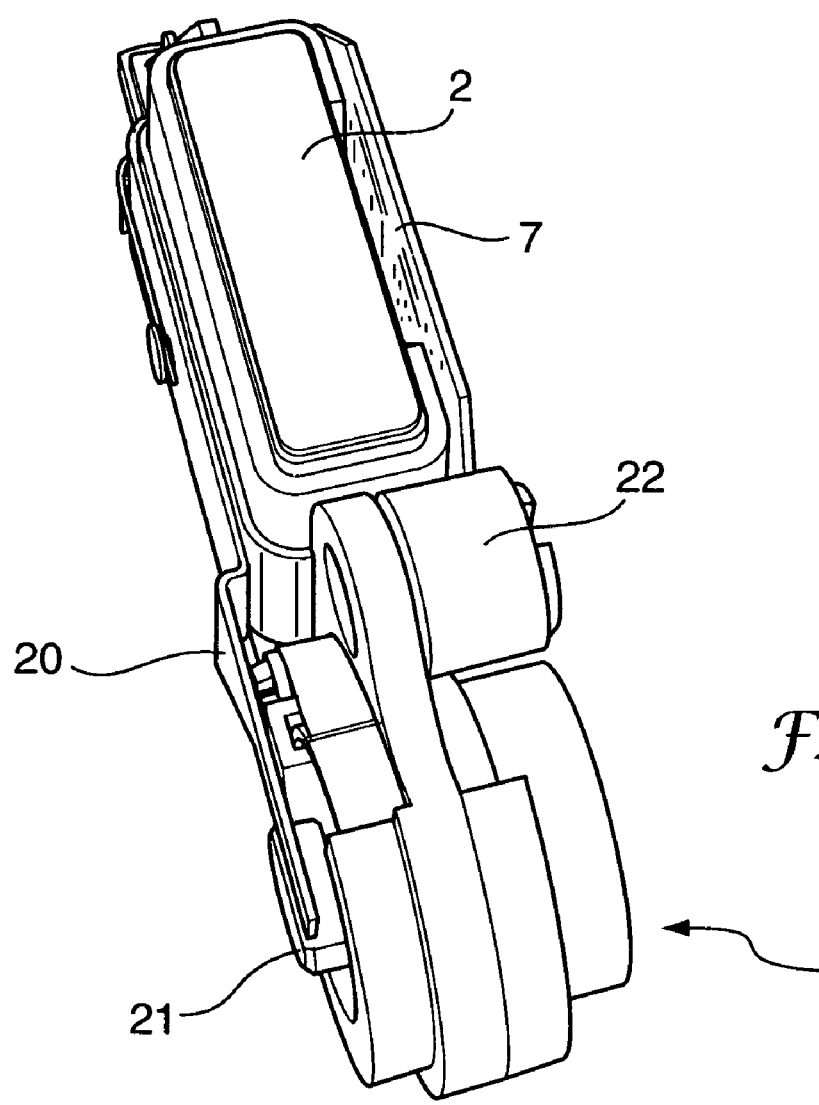
FIGS. 10 to 14 are simplified perspective views of parts of a blood glucose meter in accordance with another embodiment of the invention.
Figure 10:
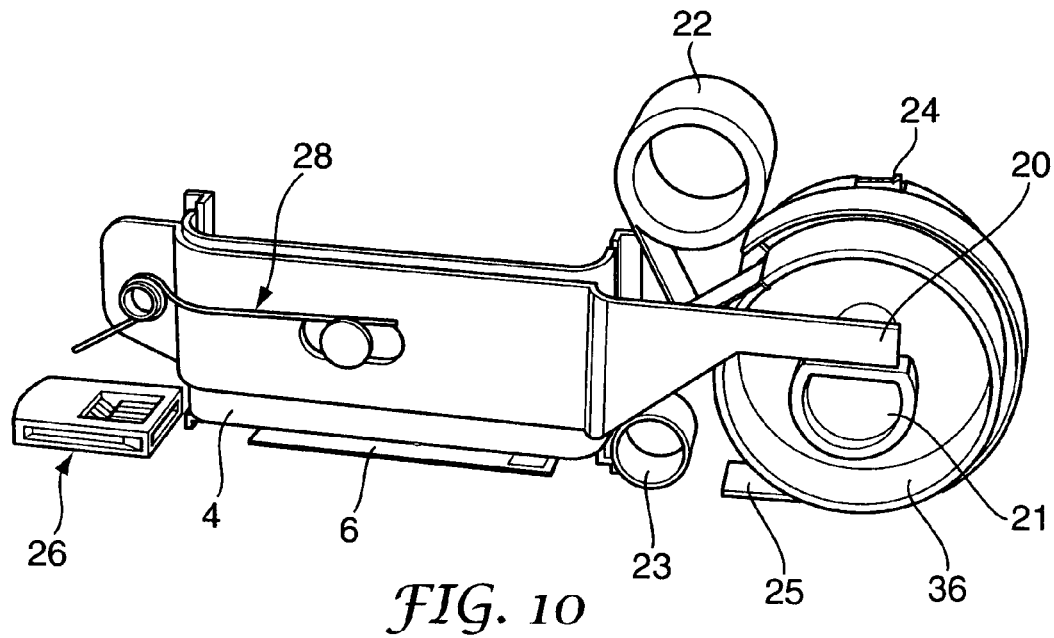
Figure 11:
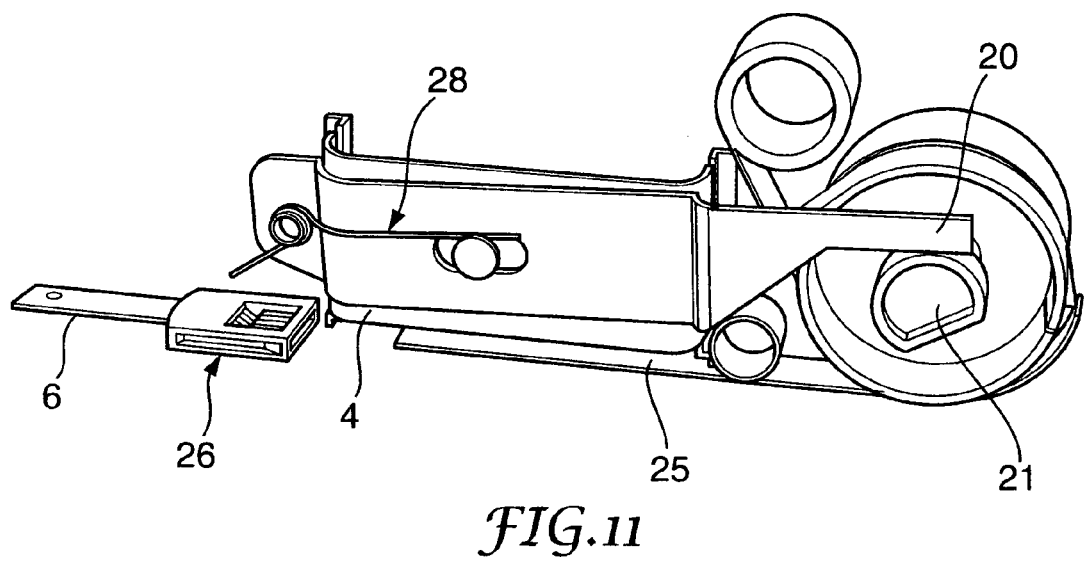
Figure 13:
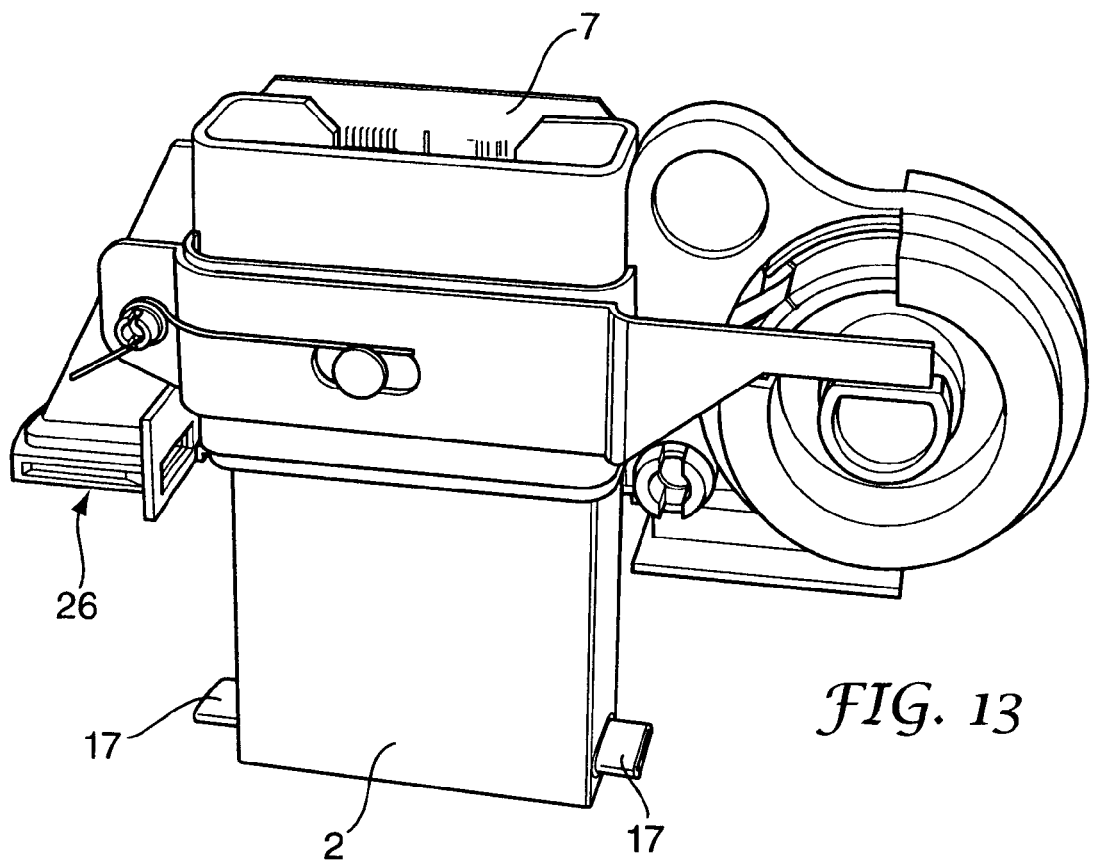
Figure 14:
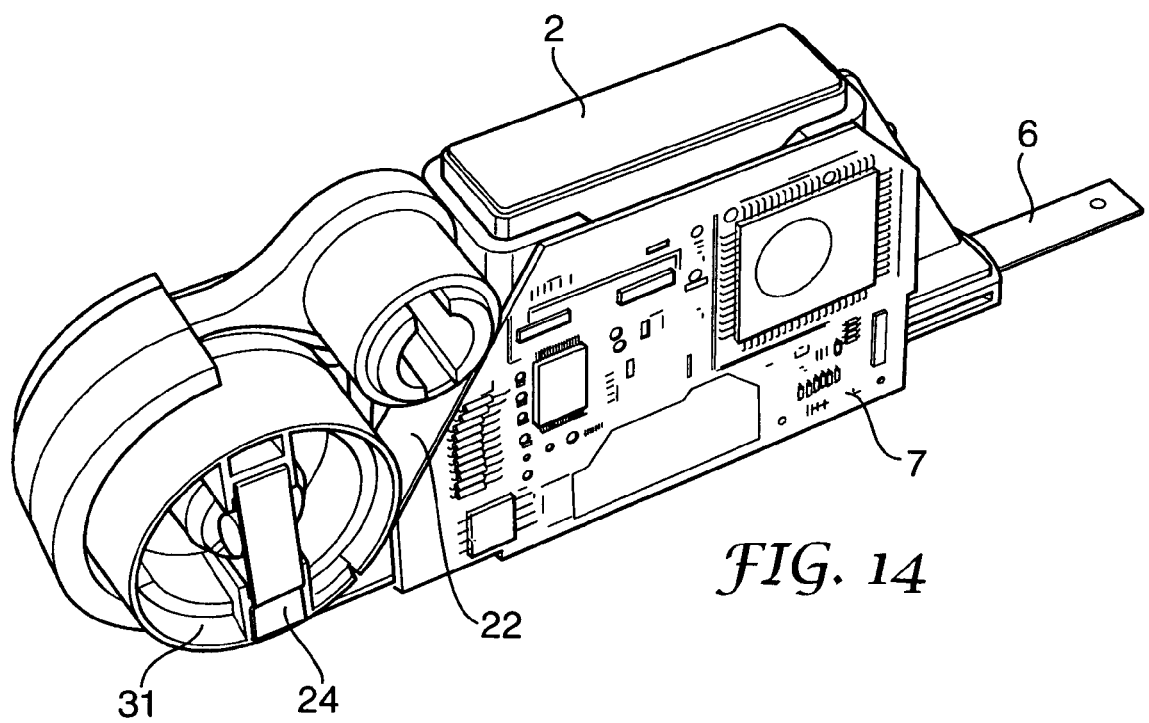

Referring now to FIG. 10, a simplified view of an alternative embodiment of the invention illustrates the location of the test strip 6 prior to being dispensed. The pusher 25 is in an undeployed state. In FIG. 11 the arm lift cam 21 has lifted the clamp arm 20 and the clamp 4. The pusher 25 has been deployed so as to push the test strip 6 to the dispensed position where its electrodes are in contact with meter contacts in the contact block 26. The pusher 25 is no longer fully deployed and is in the process of being retracted onto the pusher drum. Simplified FIGS. 12-14 illustrate parts of the meter with the cartridge 2 at different stages of insertion.

The delivery system of the meter is mechanically robust and uses simple moulded components. The mechanism permits a more symmetrical product to be manufactured because the delivery mechanism 5 sits behind the cartridge 2, as best shown in FIG. 12. The mechanism may be operated by either rotary or linear user activation. Alternative mechanical systems to control clamping of the sealing members and co-ordinated deployment of the pusher are described below with reference to FIGS. 17 and 18.

The delivery mechanism illustrated in FIG. 17 comprises drive disc 37 on which is mounted a pin 38. The drive disc 37 is connected to the arm lift dam 21 (not shown). A first transfer pinion 39 and a second transfer pinion 41 are provided with, respectively, first 40 and second 42 transfer blades. The transfer pinions 39, 41 are rotatably mounted in relation to the drive disc 37 and their teeth are interengaged. The second transfer pinion 41 is directly linked to the pusher drum 36. The mechanism works as follows.

Figure 17A:
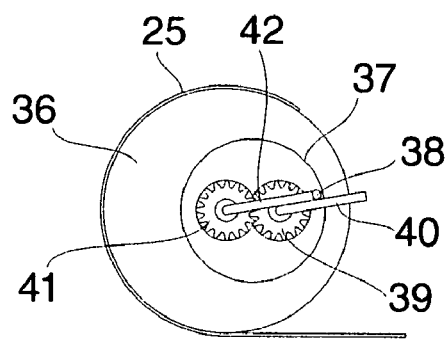
FIGS. 17 and 18 illustrate alternative drive mechanisms in accordance with still further embodiments of the invention.
Figure 17B:
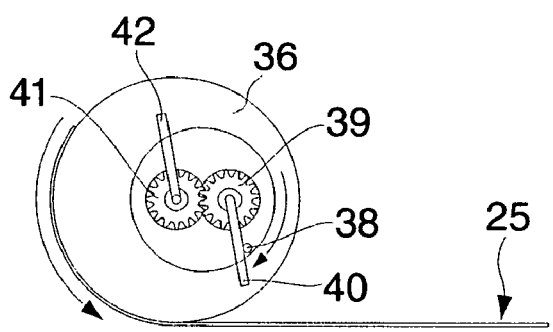
Figure 17C:
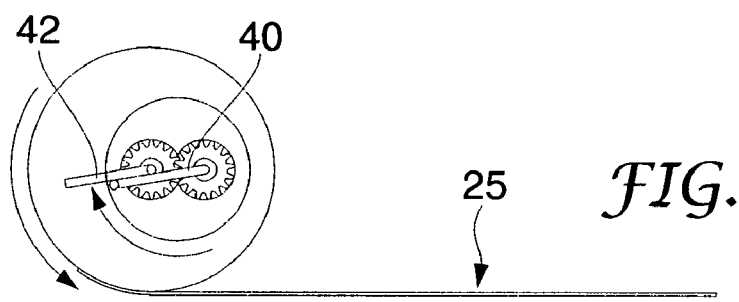
Figure 17D:
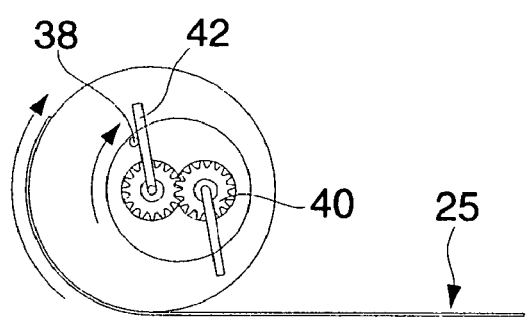
Figure 17E:
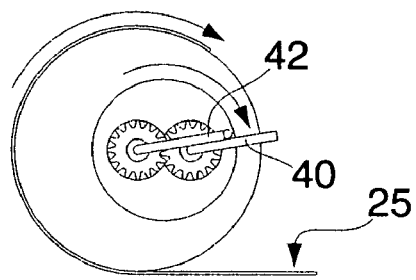

1. With the mechanism arranged as in FIG. 17a, the user winds the activating handle through 120°.
2. This action winds up the drive spring which is connected to the drive disc 37.
3. Once the user passes the "point of no return" the drive disc 37 is free to begin its 360° rotation using the energy stored in the drive spring (FIG. 17b).
4. This rotation forces the pin 38 on the drive disc 37 to push on the first transfer blade 40 which pushes the first transfer pinion 39 through 180°.
5. Pushing the first transfer pinion 39 clockwise makes the second transfer pinion 41 rotate counter-clockwise as they are directly meshed together. Turning of the second transfer pinion 41 turns the pusher drum 36 and the flexible pusher 25 is deployed (FIG. 17c) and forces a test strip to the deployed position.
6. After 180° of rotation the pin 38 slips off the first transfer blade 40 and begins to act on the second transfer pinion 41 via the second transfer blade 42. This reverses the direction of the pusher drum 36, retracting the pusher 25 (FIG. 17d).
7. At the end of the 360° rotation of the drive disc 37, the pin 38 slips off the second transfer blade 42 returning the mechanism to the rest state and completing the mechanical movement (FIG. 17e).

This system can readily be driven by an electric motor because the drive disc is driven in only one direction. Alternatively, it may be actuated by either linear or rotary user activation. It uses simple moulded components, some of which are repeated. This mechanism can also be located behind the cartridge, permitting a symmetrical product design. Because the mechanism self-reverses, no opposing spring force is required.

Figure 18A:
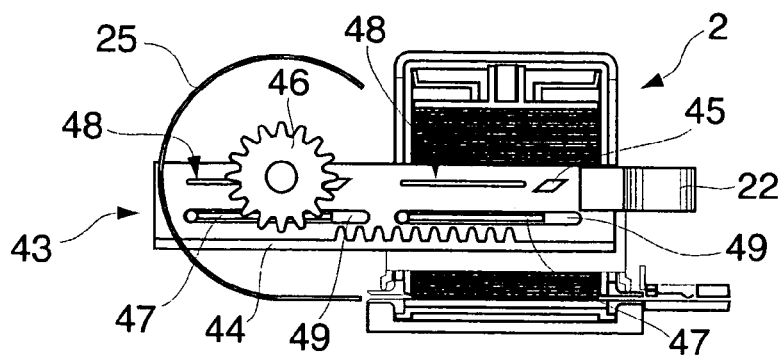
Figure 18B:
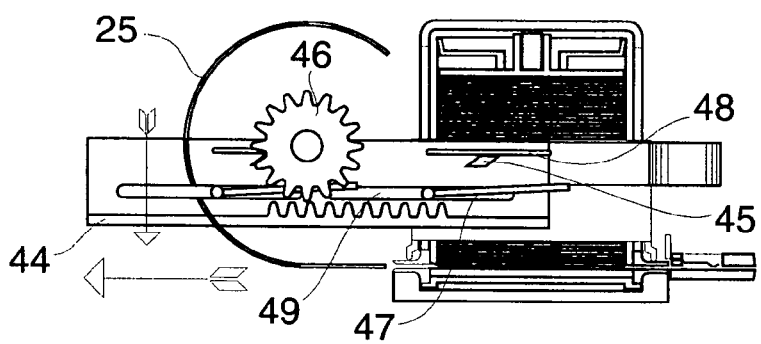
Figure 18C:
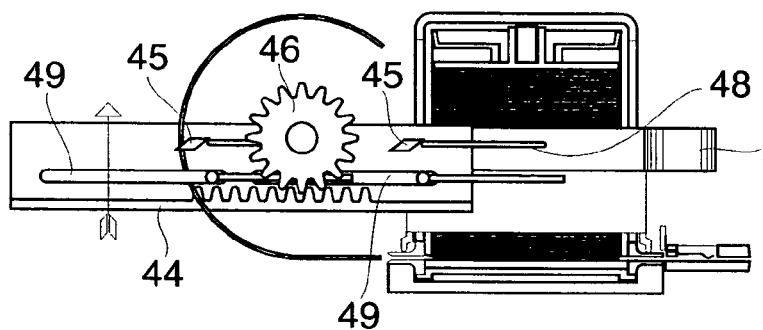
Figure 18D:
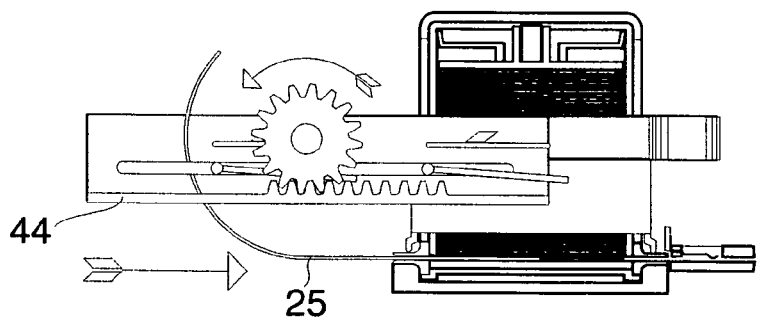
Figure 18E:
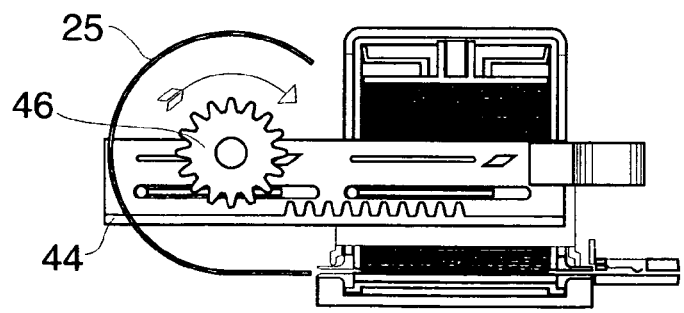

Referring now to FIG. 18, a further alternative delivery mechanism is illustrated, which uses a rack and pinion arrangement. The mechanism works as follows:

1. The user pulls back the external handle; this pulls back a slide 43 from the rest position shown in FIG. 18a and winds up the return spring. The slide 43 is provided with a rack 44 for engagement with a pinion 46.
2. As the slide 43 travels backwards, diamond-shaped lugs 45 on the slide engage with fixed ribs 48 on the chassis. The lugs 45 deflect below the ribs 48 (FIG. 18b) causing the rack 44 to miss the pinion 46. At the same time, sprung pins 47 slide in grooves 49.
3. At the position shown in FIG. 18c, the slide 43 has reached the end of its backwards travel and the lugs 45 disengage from the ribs 48, allowing the slide 43 to be pushed up by the sprung pins 47. This movement causes engagement of the rack 44 and the pinion 46.
4. The tensator spring 22 now pulls the rack (FIG. 18d), driving the pinion 46 which in turn drives the pusher drum (not shown) and deploys the pusher 25 to eject a test strip. The diamond-shaped lugs 45 now sit on the top side of the fixed ribs 48.
5. The rack 44 goes beyond the pinion 46 and a return spring withdraws the pusher 25. The lugs 45 drop off the ribs 48, leaving the mechanism in the rest position (FIG. 18e).

The mechanism is mechanically simple and uses simple moulded components.

It is appreciated that certain features of the invention, which are for clarity described in the context of separate embodiments may also be provided in combination in a single embodiment. Conversely, various features of the invention which are, for the sake of brevity, described in the context of a single embodiment, may also be provided separately or in any suitable subcombination.

Although the invention has been described with reference to a sensor dispensing device or test device for measuring blood glucose concentration, it is to be understood that the invention is not limited to this application. The invention may be used in the determination of any analyte in a fluid, biological or otherwise, by the use of suitable reagents in the test strip. Such reagents are well known to those skilled in the art.

While the present invention has been described with reference to specific embodiments, it should be understood that modifications and variations of the invention may be constructed without departing from the spirit and scope of the invention specified in the following claims.

What is claimed is:

1. A sensor dispensing device for dispensing sensors for testing of analyte concentration in a fluid to be applied thereto, the device comprising:
   a cartridge having an outer casing and a plurality of sensors arranged one upon another in a stack therein;
   a pushing member;
   the cartridge having a first dispensing end and a second opposing end spaced a fixed distance apart, and the cartridge including a first aperture for the ejection of a sensor closest to the first end and a second aperture opposed to the first aperture, for access by said pushing member;
   wherein the first aperture and the second aperture are each provided with compliant sealing means which are carried by the cartridge, said compliant sealing means are at least partly disposed outside the outer casing, the sealing means having first and second sealing surfaces which are capable of co-operating to releasably form a substantially moisture-tight seal when acted upon by suitable external clamping forces;
   the device further comprising:
   a housing for receiving the cartridge;
   for each of the said compliant sealing means, a pair of clamping members for releasably clamping the sealing means to form a substantially moisture-tight seal; and
   said pushing member reversibly inserting through the second aperture when the sealing means are not clamped, for pushing the sensor closest to the first end through the first aperture to a dispensed position.

2. A device according to claim 1, wherein each of the sealing means comprises a tube of natural or synthetic rubber.

3. A device according to claim 1, wherein each of the sealing means is formed from a thermoplastic elastomeric material.

4. A device according to claim 1, wherein the sealing means are co-moulded with the outer casing of the cartridge.

5. A device according to claim 1, wherein the outer casing of the cartridge contains an inner assembly comprising an inner casing in which is located the stack of sensors, said inner casing has opposed apertures in register with the corresponding apertures in the outer casing, for permitting entry of the pushing member and exit of a sensor.

6. A device according to claim 5, further comprising spring means within the inner casing which urge the stack of sensors towards the dispensing end, and further comprising ratchet means within the inner casing which prevent or inhibit movement of the stack of sensors towards the opposing end.

7. A device according to claim 5, wherein the cartridge inner casing is formed from a desiccant plastics material.

8. A device according to claim 1, further including a chassis connected to the housing and a delivery mechanism for deploying the pushing member from a rest position outside the cartridge to a deployed position in which said pushing member will push a sensor from the cartridge to the dispensed position.

9. A device according to claim 8, wherein the delivery mechanism further includes a pusher drum rotatably mounted on the chassis, and wherein the pushing member is flexible and is at least partly wound around the pusher drum when the sealing members are clamped.

10. A device according to claim 8, wherein actuation of the delivery mechanism to deploy the pushing member will cause unclamping of the sealing means before the pushing member enters the second aperture and wherein withdrawal of the pushing member from the deployed position to the rest position will cause clamping of the sealing means after the pushing member withdraws from the second aperture.

11. A device according to claim 10, wherein the delivery mechanism further includes a cam which is connected to the drive drum and rotatable therewith; wherein initial rotation of the cam will cause the clamping members to unclamp the sealing means, and further rotation of the cam will cause the clamping members to clamp the sealing means.

12. A device according to claim 11, wherein the delivery mechanism includes a drive drum and a drive spring connecting the drive drum and the chassis; the drive drum being rotatably mounted in relation to the pusher drum, and the drive drum being turnable by a user from an initial position so as to wind up the drive spring, and wherein the delivery mechanism further comprises latch means for releasably connecting the drive drum and the pusher drum when the drive drum has turned from its initial position to a predetermined engagement position so that returning of the drive drum from its engagement position to its initial position caused by unwinding of the drive spring will rotate the pusher drum.

13. A device according to claim 12, further including a return spring connecting the pusher drum and the chassis, wherein rotation of the pusher drum from an initial position by the drive drum will wind up the return spring so that when the pusher drum becomes disengaged from the drive drum the return spring will return the pusher drum to its initial position.

14. A device according to claim 9, wherein the delivery mechanism further comprises a first pinion wheel and a second pinion wheel and a drive member which is rotationally mounted in relation to the chassis; wherein the said pinion wheels are meshed together and one of the pinion wheels is fixed to the pusher drum so that they will rotate together; the arrangement being such that during a full rotation of the drive member it will engage with and turn the first pinion wheel for one part of its travel and will engage with and turn the second pinion wheel for a second part of its travel, whereby the pusher drum will be initially driven so as to cause the pushing member to extend from the rest position to the deployed position and will then be reversed so that the pushing member will be returned to the rest position.

15. A device according to claim 9, wherein the delivery mechanism further comprises a pinion wheel which is fixed to the pusher drum so that they will rotate together, and a rack mounted for reciprocal translation in relation to the chassis; the arrangement being such that during translation of the rack in a first direction it will not engage with the pinion and during translation of the rack in a second opposite direction it will engage with and turn the pinion so as to turn the pusher drum; the device further including a return spring connecting the pusher drum and the chassis, wherein rotation of the pusher drum from an initial position will wind up the return spring so that when the pinion becomes disengaged from the rack the return spring will return the pusher drum to its initial position.

16. A device according to claim 1, wherein the sensors comprise biosensors having reagent means thereon for producing an electrical signal in response to the concentration of analyte in an applied fluid, and electrode tracks in contact with the reagent means, and wherein the device further comprises electrical contacts mounted in relation to the housing for engaging with the said electrode tracks at the said dispensed position, and a meter connected to the contacts having electronics means for producing a signal output which is dependent on the signal from a sensor when the sensor is engaged with the contacts.

17. A sensor dispensing device for dispensing sensors for testing of analyte concentration in a fluid to be applied thereto, the device comprising:
 a cartridge having an outer casing and a plurality of sensors arranged one upon another in a stack therein;
 a pushing member;
 the cartridge having a first dispensing end and a second opposing end spaced a fixed distance apart, and the cartridge including a first aperture for the ejection of a sensor adjacent to the first end and a second aperture opposed to the first aperture, for access by a pushing member;
 wherein the first aperture and the second aperture each have disposed within them a tubular sealing member which is a close fit therefor, said tubular sealing member extends outside the outer casing, the tubular sealing members being capable of releasably forming a substantially moisture-tight seal when acted upon by suitable external clamping forces;
 the device further comprising:
 a housing for receiving the cartridge;
 for each of the said tubular sealing members, a pair of clamping members for releasably clamping the sealing means to form a substantially moisture-tight seal; said pushing member
 reversibly inserting through the second aperture when the tubular sealing members are not clamped, for pushing the sensor closest to the first end through the first aperture to a dispensed position.

18. A device for measuring analyte concentration in a fluid, comprising:

a cartridge having an outer casing and a plurality of biosensors arranged one upon another in a stack therein, each biosensor having reagent means thereon for producing an electrical signal in response to the concentration of analyte in an applied fluid, and electrode tracks in contact with the reagent means;

a pushing member;

the cartridge having a first dispensing end and a second opposing end spaced a fixed distance apart, and the cartridge including a first aperture for the ejection of a sensor closest to the first end and a second aperture opposed to the first aperture, for access by said pushing member;

wherein the first aperture and the second aperture are each provided with compliant sealing means which are carried by the cartridge, said compliant sealing means are at least partly disposed outside the outer casing, the sealing means having first and second sealing surfaces which are capable of co-operating to releasably form a substantially moisture-tight seal when acted upon by suitable external clamping forces;

the device further comprising:

a housing for receiving the cartridge;

for each of the said compliant sealing means, a pair of clamping members for releasably clamping the sealing means to form a substantially moisture-tight seal;

said pushing member reversibly inserting through the second aperture when the sealing means are not clamped, for pushing the sensor closest to the first end through the first aperture to a dispensed position; and electrical contacts mounted in relation to the housing for engaging with the said electrode tracks at the said dispensed position, and a meter connected to the contacts having electronics means for producing a signal output which is dependent on the signal from a sensor when the sensor is engaged with the contacts.

19. A cartridge having an outer casing and a plurality of sensors arranged one upon another in a stack therein, each sensor being for testing of analyte concentration in a fluid;

a pushing member;

the cartridge having a first dispensing end and a second opposing end spaced a fixed distance apart, and the cartridge including a first aperture for the ejection of a sensor closest to the first end and a second aperture opposed to the first aperture, for access by said pushing member;

wherein the first aperture and the second aperture are each provided with compliant sealing means which are at least partly disposed outside the outer casing, the sealing means having first and second sealing surfaces which are capable of co-operating to releasably form a substantially moisture-tight seal when acted upon by suitable external clamping forces.

20. A cartridge according to claim 19, wherein each of the sealing means comprises a tube of natural or synthetic rubber.

21. A cartridge according to claim 19 wherein each of the sealing means is formed from a thermoplastic elastomeric material.

22. A cartridge according to claim 19, wherein the sealing means are co-moulded with the outer casing of the cartridge.

23. A cartridge according to claim 19, wherein the outer casing of the cartridge contains an inner assembly comprising an inner casing in which is located the stack of sensors and which has opposed apertures in register with the corresponding apertures in the outer casing, for permitting entry of the pushing member and exit of a sensor.

24. A cartridge according to claim 23, further comprising spring means within the inner casing which urge the stack of sensors towards the dispensing end, and further comprising ratchet means within the inner casing which prevent or inhibit movement of the stack of sensors towards the opposing end.

25. A cartridge according to claim 22, wherein the cartridge inner casing is formed from a desiccant plastics material.

26. A cartridge according to claim 21, wherein the sealing member comprises an ethylene-propylene-diene terpolymer.

27. A cartridge according to claim 26, wherein the sealing member further comprises from 0.2 to 5% of an erucamide antistatic/slip agent.

28. A cartridge comprising a casing and a plurality of sensors arranged one upon another in a stack therein, each sensor being for testing of analyte concentration in a fluid;

a pushing member;

the casing having a first dispensing end and a second opposing end and including a first aperture for the ejection of a sensor adjacent to the first end and a second aperture opposed to the first aperture, for access by a pushing member;

tubular sealing members close fittingly disposed within each of the first and second apertures, each of the sealing members extends outside the casing, the tubular sealing members being capable of releasably forming a substantially moisture-tight seal when acted upon by suitable external clamping forces;

the cartridge further including at least one spring which urges the stack of sensors towards the dispensing end.

* * * * *